United States Patent
DePompe

(10) Patent No.: US 9,511,262 B1
(45) Date of Patent: Dec. 6, 2016

(54) FITNESS TRAINING METHOD USING UV LIGHT

(71) Applicant: Scott DePompe, Kinnelon, NJ (US)

(72) Inventor: Scott DePompe, Kinnelon, NJ (US)

( * ) Notice: Subject to any disclaimer, the term of this patent is extended or adjusted under 35 U.S.C. 154(b) by 65 days.

(21) Appl. No.: 14/741,558

(22) Filed: Jun. 17, 2015

(51) Int. Cl.
| | |
|---|---|
| *A63B 24/00* | (2006.01) |
| *A63B 69/20* | (2006.01) |
| *A63B 5/20* | (2006.01) |
| *A63B 21/06* | (2006.01) |
| *A63B 69/32* | (2006.01) |

(52) U.S. Cl.
CPC ............. *A63B 24/0075* (2013.01); *A63B 5/20* (2013.01); *A63B 21/0601* (2013.01); *A63B 69/20* (2013.01); *A63B 69/201* (2013.01); *A63B 69/205* (2013.01); *A63B 69/206* (2013.01); *A63B 69/32* (2013.01); *A63B 2024/0078* (2013.01)

(58) Field of Classification Search
CPC ... A63B 24/0075; A63B 69/20; A63B 69/206; A63B 69/201; A63B 69/205; A63B 5/20; A63B 21/0601; A63B 69/32; A63B 2024/0078
See application file for complete search history.

(56) References Cited

U.S. PATENT DOCUMENTS

| | | | |
|---|---|---|---|
| 3,649,029 A | 3/1972 | Worrell | |
| 5,743,807 A | 4/1998 | Bendo et al. | |
| 5,914,197 A | 6/1999 | Goudjil | |
| 7,089,698 B2 | 8/2006 | Afshari | |
| 7,453,418 B2 | 11/2008 | Palmquist | |
| 2007/0224583 A1 | 9/2007 | Humphrey | |
| 2008/0208296 A1* | 8/2008 | Smith | A41D 27/085 607/89 |
| 2010/0181725 A1* | 7/2010 | Smalley | A63B 24/0021 273/317.6 |
| 2012/0225739 A1* | 9/2012 | Cheshire | A63B 63/06 473/416 |
| 2013/0143684 A1* | 6/2013 | Painter | A63B 69/3614 473/220 |
| 2014/0265137 A1* | 9/2014 | Gradinger | A63B 67/06 273/400 |

* cited by examiner

*Primary Examiner* — Sundhara Ganesan
(74) *Attorney, Agent, or Firm* — Thomas J. Germinario

(57) ABSTRACT

A boxing-based fitness training regimen takes place in a training area suffusing with UV light from one or more UV light sources. Non-UV lighting in the training area is adjusted to a level of semi-darkness, in which non-luminescent objects are visible but luminescent objects clearly stand out. Multiple training regimen stations located in the training area can include heavy bag, speed bag, double-end bag, medicine ball, skip rope, shadow boxing and focus mitt regimens. Within each station, one or more items of training equipment, such as bags, gloves, hand wraps, focus mitts, medicine balls and/or jump ropes, are provided. Some or all of the training equipment at each station is UV luminescent. On some items of training equipment, there are luminescent indicia, which provide as visual cues for sequencing and/or timing of movements. These luminescent indicia can be color-coded to operate in conjunction with correspondingly color-coded visual prompts from a nearby display screen, such as an LED display. The visual prompts, in turn, can be controlled by a programmable CPU or microprocessor, so as to provide multiple alternative sequences of movements at various speeds.

6 Claims, 3 Drawing Sheets

FITNESS TRAINING METHOD USING UV LIGHT

FIELD OF INVENTION

The present invention relates to the field of fitness training and workout regimens, and more particularly to fitness training and workout regimens based on boxing-related drills and/or exercises.

BACKGROUND OF THE INVENTION

Boxing is a sport that requires a very high level of hand-eye coordination and very refined timing and sequencing of movements. It also provides a highly developed training regimen which can produce excellent physical conditioning. For those reasons, various types of fitness training regimens have been developed which draw upon drills and/or exercises associated with boxing. Such fitness regimens commonly utilize boxing-related equipment, such as boxing gloves, hand wraps, heavy bags, speed bags, double-end bags, focus mitts, medicine balls, and jump ropes.

In such boxing-related fitness regimens, precise focus on one or more moving objects is essential. But such refined focus is often difficult to achieve in a busy gym where a number of trainees are active and several persons and pieces of equipment are in motion simultaneously. Moreover, boxing fitness drills typically require an intricate series of movements executed with exact timing. Effective visual cues and prompts to coordinate such movements may also be difficult to implement in a busy gym environment.

The combined needs to focus the trainee's attention and choreograph his/her movements can be addressed by providing a semi-dark gym environment, in which ultraviolet (UV) lighting accentuates various pieces of UV-luminescent equipment and provides color-based prompts for sequencing and timing of movements. The present invention presents a training method based on such use of UV lighting.

SUMMARY OF THE INVENTION

The boxing-based fitness training regimen of the present invention takes place in a training area suffused with UV light from one or more UV light sources. Non-UV lighting in the training area is adjusted to a level of semi-darkness, in which non-luminescent objects are visible but luminescent objects clearly stand out.

Multiple training regimen stations are located in the training area. As illustrated in FIGS. 1A-1G, these stations can include heavy bag, speed bag, double-end bag, medicine ball, skip rope, shadow boxing and focus mitt regimens. Within each station, one or more items of training equipment, such as bags, gloves, hand wraps, focus mitts, medicine balls and/or jump ropes, are provided. Some or all of the training equipment at each station is UV luminescent.

On some items of training equipment, such as the heavy bag shown in FIGS. 1A and 2, there are luminescent indicia, which provide as visual cues for sequencing and/or timing of movements. As depicted in FIG. 2, these luminescent indicia can be color-coded to operate in conjunction with correspondingly color-coded visual prompts from a nearby display screen, such as an LED display. The visual prompts, in turn, can be controlled by a programmable CPU or microprocessor, so as to provide multiple alternative sequences of movements at various speeds.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

DETAILED DESCRIPTION OF THE PREFERRED EMBODIMENTS

Figure 1:
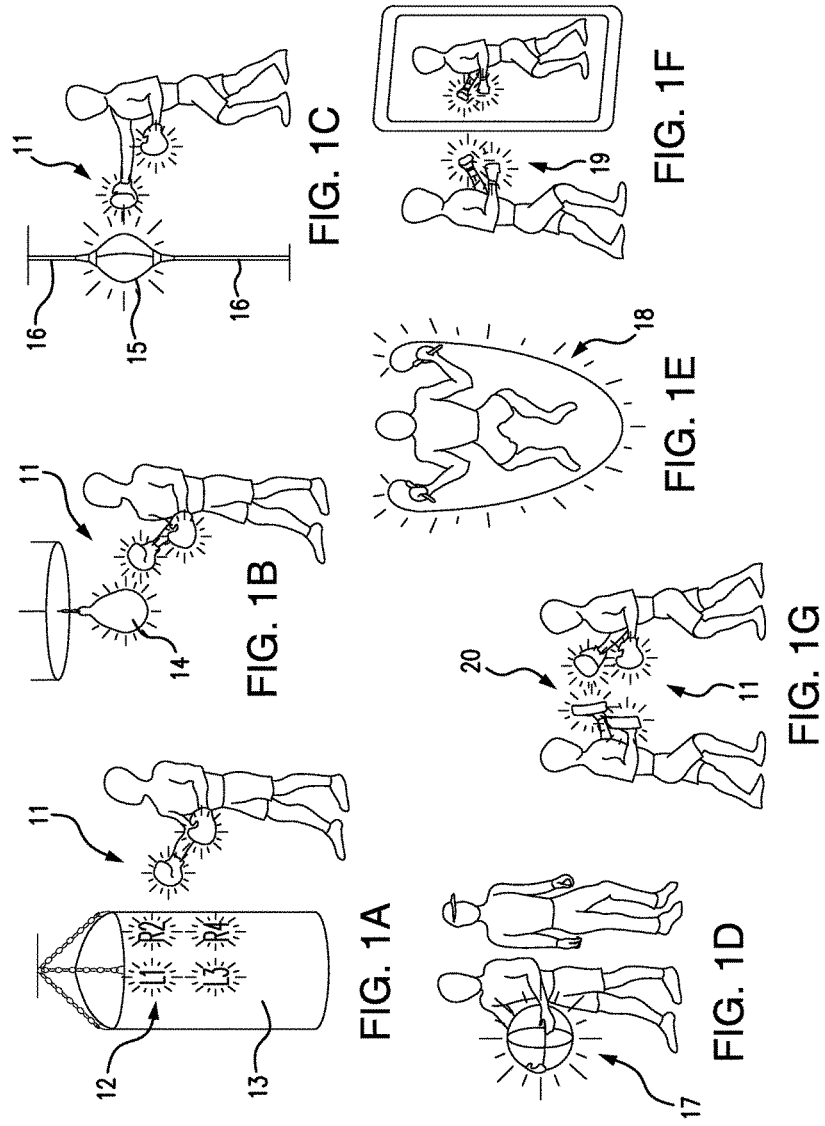
FIGS. 1A-1G depict seven exemplary training regimen stations, in accordance with one embodiment of the present invention.

Referring to FIGS. 1A-1G, an exemplary training gym/area 10 is suffused with UV light from one or more sources (not shown). Seven training regimen stations each provide one or more items of training equipment, which items can be UV-luminescent and/or incorporate UV-luminescent indicia. It should be understood that, where the use of luminous gloves 11 is indicated in FIGS. 1A-1C, luminous hand wraps 19 can also alternately be used.

The heave bag station shown in FIG. 1A provides luminescent gloves 11 and luminescent indicia 12 on the bag 13. In this example, the indicia 12 are visual cues for a sequence of punches, such as L1=left jab, R2=right cross, L3=left hook, and R4=right uppercut. The interaction of luminescent indicia 12 and gloves 11 in the eyes of the trainee serves to develop hand-eye coordination and to choreograph the punch combinations.

The speed bag station shown in FIG. 1B provides luminescent gloves 11 and a luminescent speed bag 14. In this regimen, timing is of the utmost importance, and the coordinated glow of the gloves 11 and bag 14 enable the trainee to precisely synchronize the timing of each punch with the back-and-forth motion of the bag 14.

The double-end bag station depicted in FIG. 1C provides both luminescent gloves 11 and a luminescent bag 15. Since the bag 15 is suspended between two elastic cords 16, when struck it snaps back at the trainee, compelling him to execute defensive maneuvers, akin to "slipping" a punch. The combined glow of the bag 15 and gloves 11 facilitate the timing, sequencing and alternation of punches and defensive movements.

In FIG. 1D we see an exemplary medicine ball station, in which two trainees stand back-to-back passing a luminous medicine ball 17 between them. Rapidity of passing the ball 17 is the objective of this regimen, and its luminescence improves the ability of the trainees to visually spot the ball 17 and grab it more quickly.

In FIG. 1E an exemplary jump rope station is depicted. Since footwork sequencing and timing is the objective of this regimen, the luminosity of the rope 18 renders its rapid motion easier to follow visually.

In the shadow-boxing station shown in FIG. 1F, the trainee wears luminescent hand wraps 19 as he trades punches with his mirror image. The glow of the hand wraps 19 makes it easier for the trainee to visualize his punching combinations and to time his defensive moves in response to his mirror image.

FIG. 1G shows an exemplary focus-mitt station, which provides both luminescent focus mitts 20 and luminescent gloves 11. The glow of the mitts 20 helps the trainee aim her punches at the moving targets and to "slip" the punches of the trainer. The glow of the gloves 11 helps the trainer follow the trainee's punches to see that they are properly executed and that the trainee is not dropping her defensive guard while throwing them.

Figure 2:
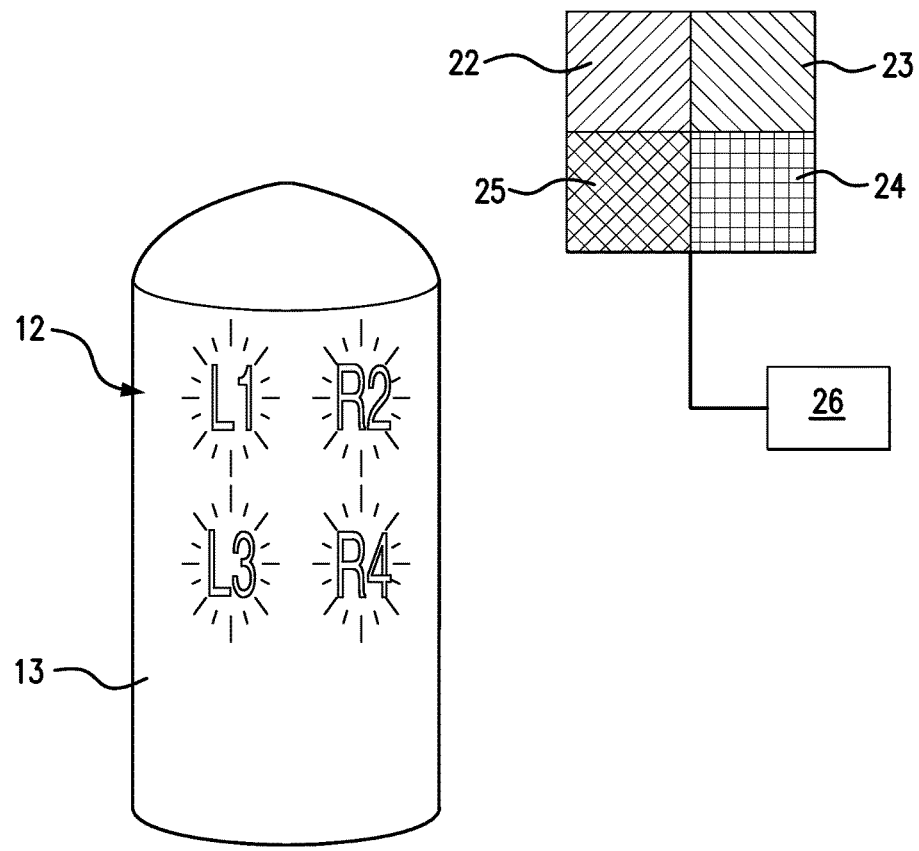
FIG. 2 depicts an exemplary heavy-bag training regimen station with color-coded indicia and a correspondingly color-coded LED prompt display controlled by a programmable CPU, in accordance with one embodiment of the present invention.

Referring now to FIG. 2, we see an exemplary heavy bag 13 containing color-coded luminescent indicia 12, which provide visual cues for a selected sequence of punches and/or combinations. In this example, the training regimen station also provides a color-coded LED display screen 21, which sequentially flashes colors corresponding to the indicia 12 on the bag 13, so as to prompt the trainee to the correct sequence and timing of punches/combinations.

For example, the quadrants of the screen 21, clockwise from the upper left, can be colored blue 22, yellow 23, green 24, and red 25, corresponding to the same colors of indicia L1, R2, R4 and L3, respectively. So the sequence blue 22, yellow 23, red 25, and green 24 on the display 21 would prompt the punch sequence L1, R2, L3, and R4, which could be a left jab, followed by a right cross, followed by a left hook, followed by a right uppercut. Two display quadrants could also flash simultaneously, calling for a combination. For example, the blue 22 and yellow 23 quadrants flashing together could call for a left jab (L1)-right cross (R2) combination.

Optionally, the display screen 21 can be controlled by a programmable CPU or microprocessor, so that a trainee can select among a number of alternate workouts involving different sequences of punches and combinations at various speeds. Such trainee selections can be made by a dedicated control module or via a smartphone application.

It should be understood that the use of display screen prompts color-coordinated with luminous colors on the training equipment is not limited to the heavy bag discussed above. For example, the four-panel display screen 21 depicted in FIG. 2 can also be used in conjunction with focus mitts 20 having luminous colors blue on the right mitt and yellow on the left mitt, and with gloves 11 having luminous colors green on the right glove and red on the left glove. Then in this scenario, simultaneous flashing of display's blue quadrant 22 and red quadrant 25 would call for the trainee to punch the trainer's right mitt with his/her left glove.

Figure 3:
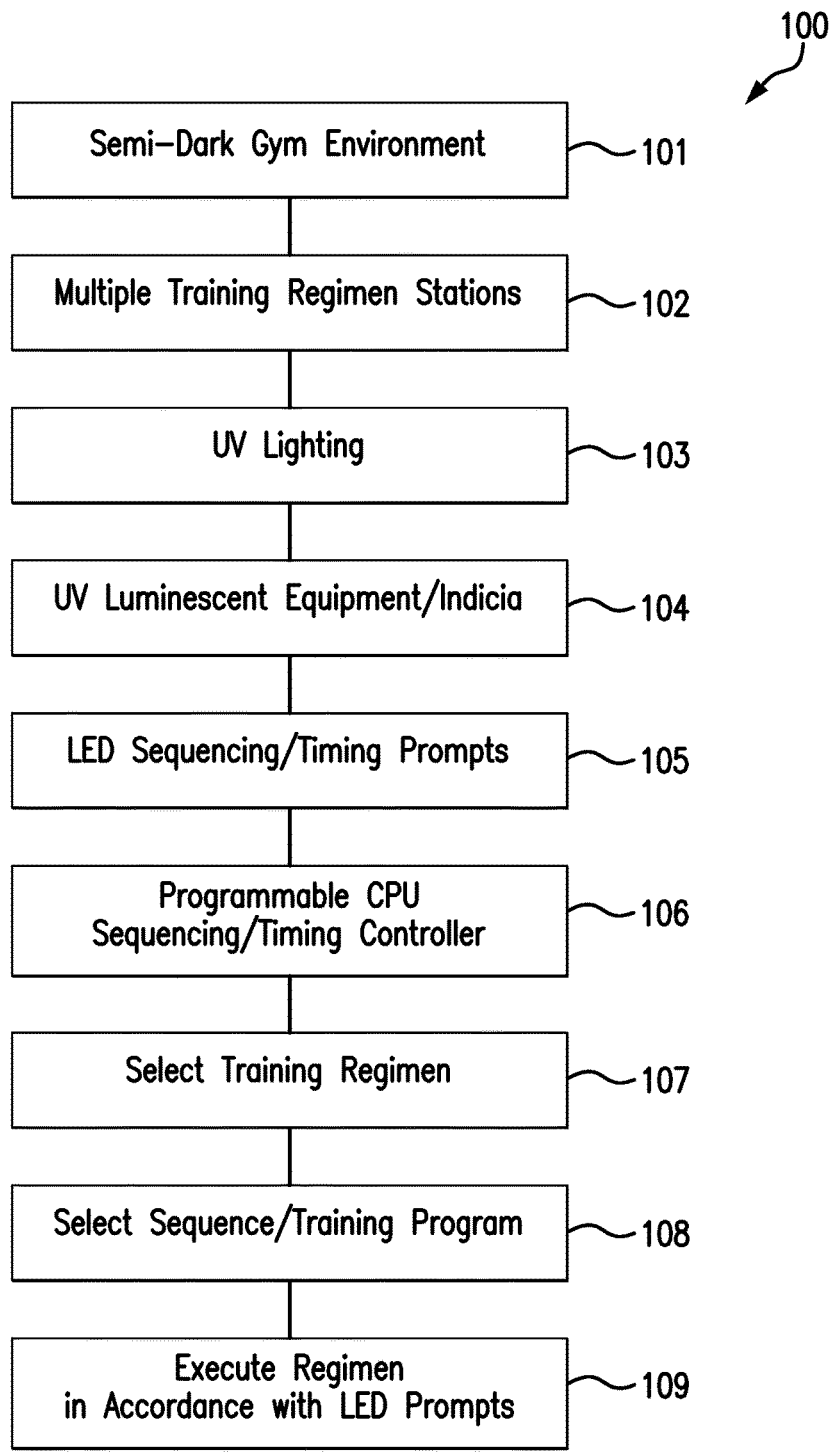
FIG. 3 is a flow chart illustrating an exemplary boxing-based fitness training method, in accordance with one embodiment of the present invention.

Referring to FIG. 3, an exemplary boxing-based fitness training method 100 comprises the first step of providing a semi-dark gym environment 101, with sufficient non-UV light to make non-luminescent objects visible without diminishing the brightness of the luminescent training equipment. The second step provides multiple training regimen stations 102, such as those depicted in FIGS. 1 and 2. The third and fourth steps provides one or more UV light sources 103 and UV luminescent equipment and/or indicia 104.

The fifth step provides LED sequencing and timing prompts 105, which are color-coordinated with the luminescent indicia on certain items of training equipment, while the sixth step provided a programmable CPU controller 106 for the LED prompts.

In the seventh and eighth steps of the method, the trainee selects a training regimen 107 and then selects a sequence/timing program 108 from among those afforded by the CPU controller. After the regimen and program are selected, the trainee executes the regimen in accordance with the LED prompts 109.

Although the preferred embodiments of the present invention have been disclosed for illustrative purposes, those skilled in the art will appreciate that many additions, modifications and substitutions are possible, without departing from the scope and spirit of the present invention as defined by the accompanying claims.

What is claimed is:

1. A method of fitness training, comprising the following steps:
 (a) providing a training area containing one or more training regimen stations;
 (b) providing in each training regimen station one or more items of training equipment, wherein one or more of the items of training equipment are UV luminescent items which are entirely UV luminescent or contain one or more UV luminescent areas;
 (c) suffusing some or all of the training area with UV light from one or more UV light sources;
 (d) conducting one or more training regimens at one or more of the training regimen stations, wherein each of the training regimens requires a sequence of training movements, and wherein each training movement requires a specific movement timing; and
 (e) prompting the sequence of training movements and the movement timing by the interaction of the UV light with the UV luminescent items.

2. The method of claim 1, comprising the following additional steps, between step (c) and step (d):
 (c1) suffusing some or all of the training area with non-UV light, from one or more non-UV light sources;
 (c2) adjusting the non-UV light to a level of semi-darkness, in which non-UV-luminescent objects are visible, but less visible than the UV luminescent items.

3. The method of claim 2, wherein one or more of the UV luminescent areas comprise UV luminescent indicia, and wherein the UV luminescent indicia signify the sequence of training movements.

4. The method of claim 3, comprising the following additional steps after step (e):
 (f) configuring the UV luminescent indicia so that each of the indicia glows with a distinct luminous indicia color when illuminated by the UV light; and
 (g) prompting the sequence of training movements by a corresponding sequence of luminous indicia colors.

5. The method of claim 4, comprising the following additional steps after step (g):
 (h) providing, in proximity to some or all of the training regimen stations, one or more displays, which are configured to emit a sequence of display colors, corresponding the luminous indicia colors, at specific display intervals; and
 (i) prompting the sequence of training movements by the sequence of display colors; and
 (j) prompting the movement timing by the display intervals.

6. The method of claim 5, comprising the following additional steps after step (j):
 (k) controlling the sequence of display colors and the display intervals with a programmable CPU or microprocessor; and (l) configuring the CPU or microprocessor to enable multiple alternative sequences of training movements at multiple alternatives of movement timing.

\* \* \* \* \*